(12) United States Patent
Kesling (10) Patent No.: US 9,113,984 B2
(45) Date of Patent: Aug. 25, 2015

(54) POD FOR SHIPPING PREPASTED ORTHODONTIC APPLIANCES

(71) Applicant: TP Orthodontics, Inc., LaPorte, IN (US)

(72) Inventor: Andrew C. Kesling, Lakeside, MI (US)

(73) Assignee: TP ORTHODONTICS, INC., La Porte, IN (US)

( * ) Notice: Subject to any disclaimer, the term of this patent is extended or adjusted under 35 U.S.C. 154(b) by 0 days.

(21) Appl. No.: 13/945,543

(22) Filed: Jul. 18, 2013

(65) Prior Publication Data

US 2015/0021210 A1    Jan. 22, 2015

(51) Int. Cl.
| | |
|---|---|
| *A61B 19/02* | (2006.01) |
| *A61C 19/02* | (2006.01) |
| *B65D 75/58* | (2006.01) |
| *B65B 5/04* | (2006.01) |
| *A61C 7/14* | (2006.01) |

(52) U.S. Cl.
CPC . *A61C 19/02* (2013.01); *B65B 5/04* (2013.01); *B65D 75/5855* (2013.01); *A61C 7/14* (2013.01); *A61C 2202/00* (2013.01)

(58) Field of Classification Search
CPC .......... A61C 19/10; A61C 19/02; A61C 7/12; A61C 7/303; A61C 2201/011; B65D 81/022; A61B 2019/0201; A61B 2019/0265; A61B 2019/00
USPC ......... 206/368, 369, 461, 462, 469, 813, 438, 206/460, 63.5, 558, 564, 588, 0.82, 751, 206/752, 754, 756, 764, 477–483, 493; 433/3, 8–17, 24
See application file for complete search history.

(56) References Cited

U.S. PATENT DOCUMENTS

| | | | |
|---|---|---|---|
| 3,574,942 A * | 4/1971 | McCabe | 433/14 |
| 4,204,325 A | 5/1980 | Kaelble | |
| 4,392,569 A * | 7/1983 | Shoup | 206/5.1 |
| 4,948,367 A | 8/1990 | Haas | |
| 4,978,007 A | 12/1990 | Jacobs et al. | |
| 4,979,611 A | 12/1990 | Bolliger et al. | |
| 5,172,809 A | 12/1992 | Jacobs et al. | |
| 5,183,403 A | 2/1993 | Masuhara et al. | |
| 5,221,202 A | 6/1993 | James | |
| 5,328,363 A * | 7/1994 | Chester et al. | 433/9 |
| 5,348,154 A | 9/1994 | Jacobs et al. | |
| 5,354,199 A | 10/1994 | Jacobs et al. | |
| 5,429,229 A | 7/1995 | Chester et al. | |
| 5,538,129 A | 7/1996 | Chester et al. | |
| 5,575,645 A | 11/1996 | Jacobs et al. | |
| 5,636,736 A | 6/1997 | Jacobs et al. | |
| 5,759,028 A | 6/1998 | Bozman | |
| 5,762,192 A | 6/1998 | Jacobs et al. | |
| 5,827,058 A | 10/1998 | Kelly et al. | |

(Continued)

*Primary Examiner* — Anthony Stashick
*Assistant Examiner* — James M Van Buskirk
(74) *Attorney, Agent, or Firm* — Cook Alex Ltd.

(57) ABSTRACT

A pod for shipping a prepasted orthodontic appliance including a compartment having a cover or lid. The appliance includes uncured adhesive on its base and is removably attached to the underside of the lid and removable from the pod upon lifting of the lid. It is thereafter removable from the cover for placement on a tooth. The appliance is removably mounted on the lid by a compressible element frictionally engagable with an opening or openings of the appliance. When the lid is in closed position the appliance is suspended above the bottom of the pod so that the uncured adhesive does not touch the interior walls of the pod.

12 Claims, 4 Drawing Sheets

(56) References Cited

U.S. PATENT DOCUMENTS

| | | |
|---|---|---|
| 6,089,861 A | 7/2000 | Kelly et al. |
| 6,183,249 B1 | 2/2001 | Brennan et al. |
| 6,482,003 B2 | 11/2002 | Dixon et al. |
| 6,786,720 B1 | 9/2004 | Kesling et al. |
| 6,834,761 B1 | 12/2004 | Kesling |
| 6,843,370 B2 | 1/2005 | Tuneberg |
| 6,960,079 B2 | 11/2005 | Brennan et al. |
| 7,381,053 B2 | 6/2008 | Tuneberg |
| 7,469,783 B2 | 12/2008 | Rose, Sr. |
| 7,726,470 B2 | 6/2010 | Cinader, Jr. et al. |
| 2005/0016884 A1 | 1/2005 | Stout et al. |
| 2010/0311004 A1* | 12/2010 | Voudouris ............... 433/11 |
| 2013/0075282 A1* | 3/2013 | Cinader et al. ............ 206/63.5 |

* cited by examiner

POD FOR SHIPPING PREPASTED ORTHODONTIC APPLIANCES

TECHNICAL FIELD

This invention relates to a new and improved package or pod for shipping and or storing prepasted orthodontic appliances and particularly prepasted orthodontic brackets so that the appliance can be shipped to and/or stored by a user with uncured adhesive on the base of the appliance for immediate mounting on a tooth. One or more pods may be provided depending upon how the appliance or appliances are shipped to a user. Where multiple pods are provided, each is capable of receiving a prepasted appliance that is suspended from the lid or cover of the pod. A compressible element or elements are secured to the cover of the lid at the underside for frictionally engaging an appliance to suspend the appliance within the pod compartment when the lid is closed and retain the appliance within the pod such that the adhesive does not touch the walls or cover of the pod.

BACKGROUND OF THE INVENTION

Heretofore it has been well known to provide pods or packages for shipping and/or storing of prepasted orthodontic appliances such as brackets and the like.

Pods for shipping of prepasted brackets are shown in U.S. Pat. No. 4,978,007 and particular in FIGS. 9 and 11. The embodiment in FIG. 9 shows a prepasted bracket engaging the bottom of the pod while the embodiment of FIG. 11 shows a prepasted bracket having an alignment device or a jig connected to the bracket to suspend the bracket above the base of the pod so that the adhesive on the back of the bracket does not touch the bottom or walls of the pod. Other prior art patents showing the packaging of a prepasted orthodontic appliance or bracket in a pod include U.S. Pat. Nos. 4,979,611, 5,221,202, 5,328,363, 5,348,154, 5,538,129, 5,762,192, 6,960,079, 7,381,053 and 7,726,470. With respect to prior known pods where the prepasted bracket engages the bottom of the pod it is always possible to leave a portion of the bonding material in the pod when removing the appliance from the pod and in those cases insufficient bonding material may be left on the appliance to compromise the bond of the appliance to a tooth.

With respect to pods having means for supporting and suspending the prepasted appliance above the bottom of the pod such as by means of a jig or alignment device, there are many clinicians that do not favor having a jig mounted on the bracket when transferring the bracket from a pod to a tooth after which the jig must be removed. It is preferred to just have the bracket jigless which would facilitate the speed of mounting the bracket on a tooth and not having to remove the jig from the bracket once it is on a tooth. Moreover, sometimes that becomes an issue relative to proper placement of a bracket on a tooth, particularly when the adhesive is uncured and must thereafter be cured.

It has also been known to provide a pod where the bracket is spaced on the very bottom of the pod on upstanding ridges as shown in U.S. Pat. No. 5,221,202 but this pod is objectionable in as much as it does not include means within the pod to prevent the pod from moving within the pod during shipping and/or storing where the bonding material on the base of the appliance may be disturbed and/or minimized, thereby compromising the bond on the tooth, and merely resting the uncured adhesive on the ridges tends to disturb the adhesive layer.

It will be appreciated that some heretofore otherwise known pods or containers for prepasted appliances are such that disturbance of the uncured adhesive or removal of portions of the adhesive will impair the integrity of the bond on the tooth. The prior art showing pods with supporting structures to engage in areas between the tie wings and the base include U.S. Pat. Nos. 6,089,861 and 7,381,051. However, these pods do not have the supporting structure connected to the lid or cover of the pod and therefore opening of the lid does not also retrieve the prepasted appliance from the pod for easy handling by the user for mounting the appliance on a tooth. As above mentioned jig mounted prepasted appliances as shown in U.S. Pat. Nos. 5,172,809 and 7,469,783, while suspending a prepasted appliance within a pod, require removal from the pod by engaging the jig, and after the appliance is mounted on a tooth it is necessary to ultimately remove the jig from the bracket before it can be used in a system.

SUMMARY OF THE INVENTION

The package of the invention which comprises a pod having means on the lid for suspending or supporting a prepasted appliance within the pod and preventing the prepasted base from engaging any of the pod walls. It is thereby only necessary for the user to open the pod by lifting the flexible lid which withdraws the appliance from the pod compartment so that it can easily be grasped by forceps or a tweezer and removed from the lid. Thereafter the appliance may be mounted on a tooth by a user so that the user can cure the bondable adhesive and properly bond the appliance to a tooth.

The pod of the invention may be supplied either in singular or in multiple arrangements, whereby it can either be used to ship a single prepasted appliance or multiple prepasted appliances for a particular patient. The prior art does not teach or suggest the frictional mounting of a prepasted appliance onto the lid of a pod whereby opening of the pod by lifting the lid withdraws the appliance from the pod so that it may be removed from the lid and then immediately mounted on a tooth. The lid of the pod of the invention includes an attaching element of a suitable compressible material that frictionally retains the appliance by engaging the archwire slot of a bracket or into the spaces between the tie wings and the base of the bracket. With respect to other prepasted appliances the attaching compressible element on the lid is configured to releasably engage the appliance to support it in the compartment of the pod such that it can easily be separated from the lid when the lid is opened, and thereafter mounted on a tooth.

Once a prepasted appliance is removably attached to a lid by a compressible member and thereafter the lid is closed to place the prepasted device within the pod, it would be appreciated that the prepasted appliance remains in place and suspended so that the uncured adhesive on its base will not engage or touch the inner walls of the pod. Accordingly the adhesive will not be disturbed or removed from the appliance during shipping and/or storing of the appliance in the closed pod to ultimately assure proper bonding on a tooth.

It will be appreciated that the material of a pod is opaque to any curing light energy so as to not cause curing of a light curable adhesive while in the pod. Likewise chemically activating or thermally activating adhesive will not be disturbed and will come out of the pod intact for later mounting on a tooth. Accordingly the bonding strength of the bonding material will be maximized once it is mounted on a tooth and properly cured. As above mentioned, while the bonding material may be chemically or heat activated, it normally will be light energy activated.

While the pod of the invention is generally used for prepasted orthodontic brackets it will be appreciated that it could be used for other prepasted orthodontic appliances such as buccal tubes or lateral attachments. In any case the pod is especially useful for prepasted appliances having light curable adhesive and accordingly the material for making the pod is such that it will transmit light energy that would cause curing of the uncured adhesive. Thus the pod protects a prepasted appliance having a layer of uncured adhesive during shipment from the manufacturer to the user and/or for storage at the user's location.

The package for prepasted brackets of the present invention includes one or more pods formed to receive a prepasted orthodontic appliance and particularly a bracket. The pod is provided with means for resiliently or compressibly frictionally engaging a bracket and mounting it on the lid of the pod. Accordingly the appliance will be moved into and out of the pod by the manipulation of the lid between open and closed positions. So when it is desired to use a particular appliance in a pod, the cover or lid is lifted from the pod which withdraws the appliance from the pod for purposes of then being removed from the cover and applied directly to a tooth. When the prepasted appliance is within the pod it is completely sealed from the outside atmosphere and held such that the uncured adhesive on the base of the appliance will not engage any of the internal walls of the pod compartment.

Accordingly the pod of the invention serves to protect a prepasted orthodontic appliance having an uncured layer of adhesive on the base during shipment from the manufacturer to the user. Normally the adhesive used on a prepasted bracket is light curable. It should be appreciated that other uncured adhesives may be used that are chemically or thermally curable and will serve to properly bond an appliance to the teeth of a patient.

Any suitable light curable polymer resin or bonding adhesive may be used on the appliances such as the Python Light Cured Adhesive sold by TP Orthodontics, Inc. of LaPorte, Ind. Python is a trademark owned by TP Orthodontics, Inc. A suitable activator curable type adhesive would be the Python One Step Adhesive or the Right On No Mix Adhesive also sold by TP Orthodontics, Inc. Python One Step and Right On are trademarks owned by TP Orthodontics, Inc.

Accordingly where a reference is made to a polymer resin on the base of an appliance, such as a bonding adhesive, it is intended to relate to any suitable light, heat or chemically curable adhesive for bonding appliances to teeth.

The pod of the present invention may be in the form of a single pod for a single prepasted orthodontic appliance or in a multiple arrangement on a carrier where an entire system is set up for a patient. Each pod includes a cover member or lid for purposes of closing the pod after a prepasted appliance is mounted on the lid and ready to be inserted into the pod compartment. The pods on the carrier and cover or lid of the pods are of an opaque material so as to prevent light energy or actinic radiation from entering the pod during the time the prepasted appliance is shipped to a user and/or stored to prevent partial or complete curing of any light curable adhesive or the disturbance of the adhesive otherwise. On the underside of the lid or cover of the pod, means Is provided in order to resiliently attach or connect the bracket to the lid and suspend the appliance within the compartment of the pod such that the base of the appliance which is prepasted will not engage the walls of the pod. Basically the appliance will be suspended in the pod so that the adhesive on the base will not engage any of the interior walls of the pod.

The means employed for mounting a prepasted appliance onto the underside of a lid or cover includes either a bar of compressible material engagable in the archwire slot of a bracket or other opening of a particular appliance. Alternately the engagable means may be in the form of compressible hanging members engagable in the spaces between the tie wings and the base of a bracket. Where the pod is otherwise used to ship other appliances such as a buccal tube, a member would be extending from the underside of the lid and resiliently engaging into the opening of the buccal tube to retain the buccal tube in position while in the pod when the cover is closed, thereby keeping the uncured adhesive on the base of the appliance from engaging the inner walls of the pod. It will be appreciated that where other types of prepasted appliances are provided any suitable means will be provided to resiliently engage the appliance such as to mount it on the underside of the lid of the pod.

It will be appreciated that one end of the lid will be permanently attached by a suitable adhesive to the upper side of the pod to provide a hinge for allowing the lid to be raised and/or lowered, in connection with securing the lid to the pod by a repositionable adhesive. Thus a repositionable pressure sensitive adhesive is used to normally keep the lid closed during shipping and/or storing of a prepasted appliance within the pod.

The pod may take any suitable shape such as to receive the appropriate prepasted appliance and carry it within the pod during shipping and/or storage. The pod may be circular in shape, square in shape, rectangular in shape or oblong in shape. It will also be appreciated that the uncured adhesive on the prepasted appliance will be tacky so that once the appliance is removed from the pod lid it can be initially placed in position on a tooth and thereafter the adhesive would be cured according to whether it was a light curable adhesive, a thermally curable adhesive or a chemically curable adhesive.

It is therefore an object of the present invention to provide a new and improved pod for shipping and/or storing prepasted appliances that includes a container of substantially rigid material with a cover of flexible material, where the prepasted appliance is frictionally mounted on means attached to the underside of the cover so that opening of the cover withdraws the appliance from the container for removal from the cover and mounting on a tooth of a patient.

Other objects, features and advantages of the invention will be apparent from the following detailed disclosure, taken in conjunction with the accompanying sheets of drawings, wherein like references numerals refer to like parts.

DETAILED DESCRIPTION OF THE INVENTION

The pod of the invention is a new and improved pod in that it provides a shipping container for a prepasted orthodontic appliance wherein the uncured adhesive on the appliance is maintained in spaced relation to the interior walls of the pod so that it will not be disturbed during shipping or storing of the appliance in the pod. Heretofore it was common to either allow the adhesive of a prepasted appliance to engage the bottom of the pod or resting on supports mounted on the bottom wall of the pod. The invention here is to avoid any engagement of the uncured adhesive with the interior walls of the pod or any supports whereby the prepasted appliance is supported from the lid or cover of the pod and suspended above in spaced relation to the walls of the pod. Accordingly when the lid or cover is lifted to open the pod it also withdraws the prepasted appliance for access by a user. Thereafter the appliance may be removed from the cover and directly mounted onto a tooth.

The prepasted appliance in the pod of the present invention is removeably attached to the underside of the lid by compressible or resilient means engaging either in an opening of the appliance or around certain areas of the appliance to hold it in place. Where an orthodontic bracket is shipped, in one embodiment a bar extends from the underside of the lid and is compressibly engaged in the archwire slot of the bracket to frictionally retain the bracket in place on the lid. In another embodiment, multiple compressible members are provided to engage different parts of the prepasted appliance such as two members that frictionally engage between the tie wings and the base of an orthodontic bracket. Where a prepasted buccal tube is shipped a hanging member attached to the underside of the lid will be shaped to engage in the opening of the buccal tube in hold it in place against the lid.

The pod of the invention may be in singular form or it may be in multiple form depending upon how the manufacture is shipping either one or multiple appliances to a customer. Thus the pods could be individual and then inserted into openings on a carrier and arranged so that multiple appliances could be provided in one situation.

While the pod of the invention is illustrated in the drawings as being elongated or oblong in shape, it may be appreciated that it could be a circular pod or a square or rectangular pod if so desired. The pod would particularly be of a type that could ship multiple type of prepasted appliances if so desired. In that case there would only be a difference in the type of retention of means on the lid or cover of the pod to which the appliance would be removably retained. Further, one pod may be sized to hold multiple appliances.

It should be appreciated that the pod may be made of any suitable plastic or resinous material including a suitable polystyrene or vinyl or polypropylene that may be easily shaped by molding, thermoforming or the like into the desired shape of the pod.

It will be understood that the prepasted appliance illustrated herein is an orthodontic bracket having a layer of uncured adhesive or bonding material on the base which thereafter may be cured depending on the type of bonding material used. Also illustrated is a prepasted buccal tube. For example, if the bonding material is a light curable adhesive which would be normally be used on brackets, it can be cured by subjecting the adhesive to a curing light. If it is a chemically curable material, it may be subjected to the use of a certain chemical in order to cause a layer to cure. Or it could be a thermally sensitive material whereby it could be cured by the application of heat.

Figures 1, 2:
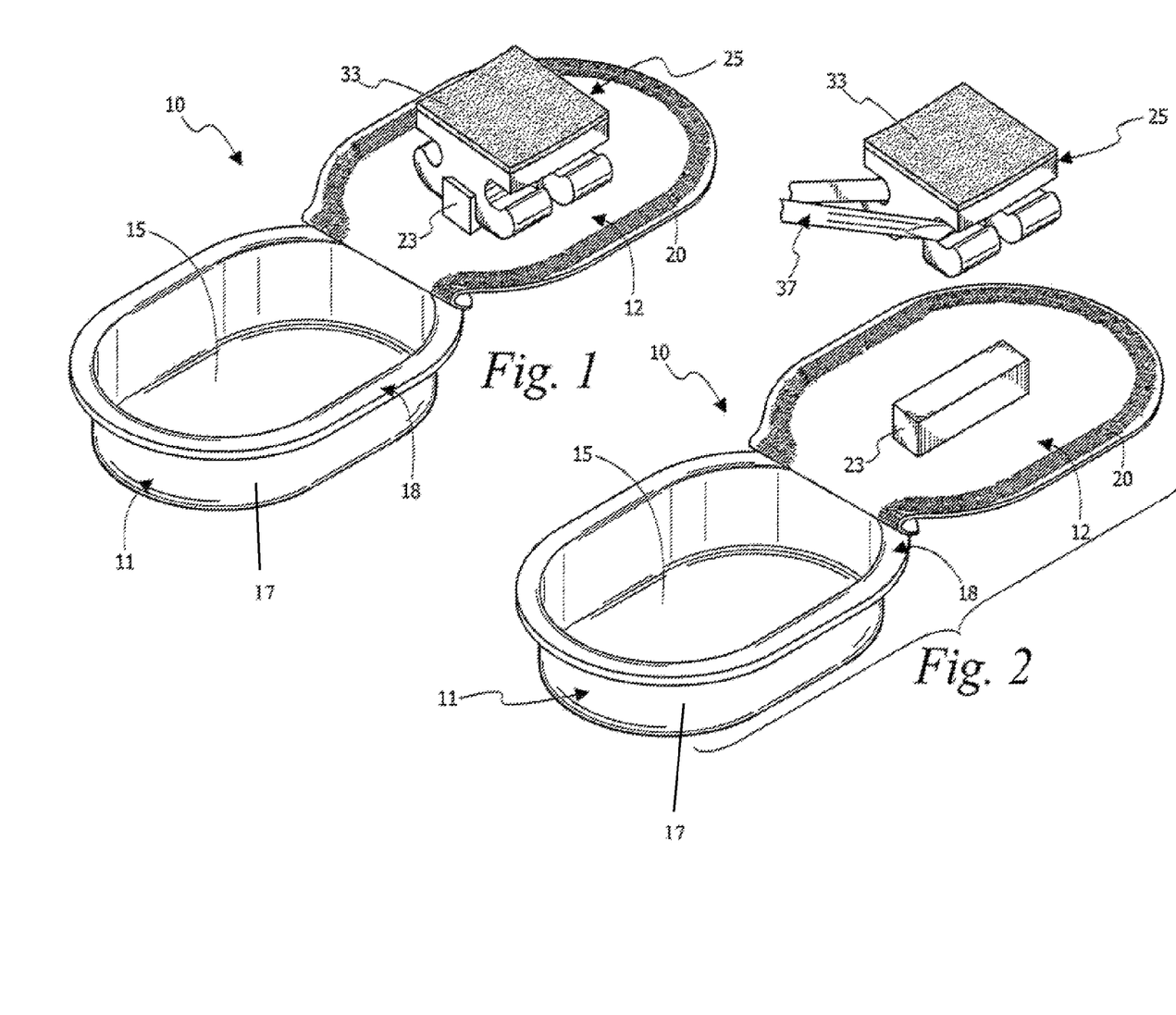
FIG. 1 is an enlarged perspective view of a pod having a bracket mounted on the underside of the lid according to the invention and where the lid is shown in open position to provide access to the appliance and removal from the lid.
FIG. 2 is an enlarged exploded perspective view of FIG. 1 wherein a broken view of an instrument engages the appliance and may be removed from the lid retaining means.
Figures 3, 4:
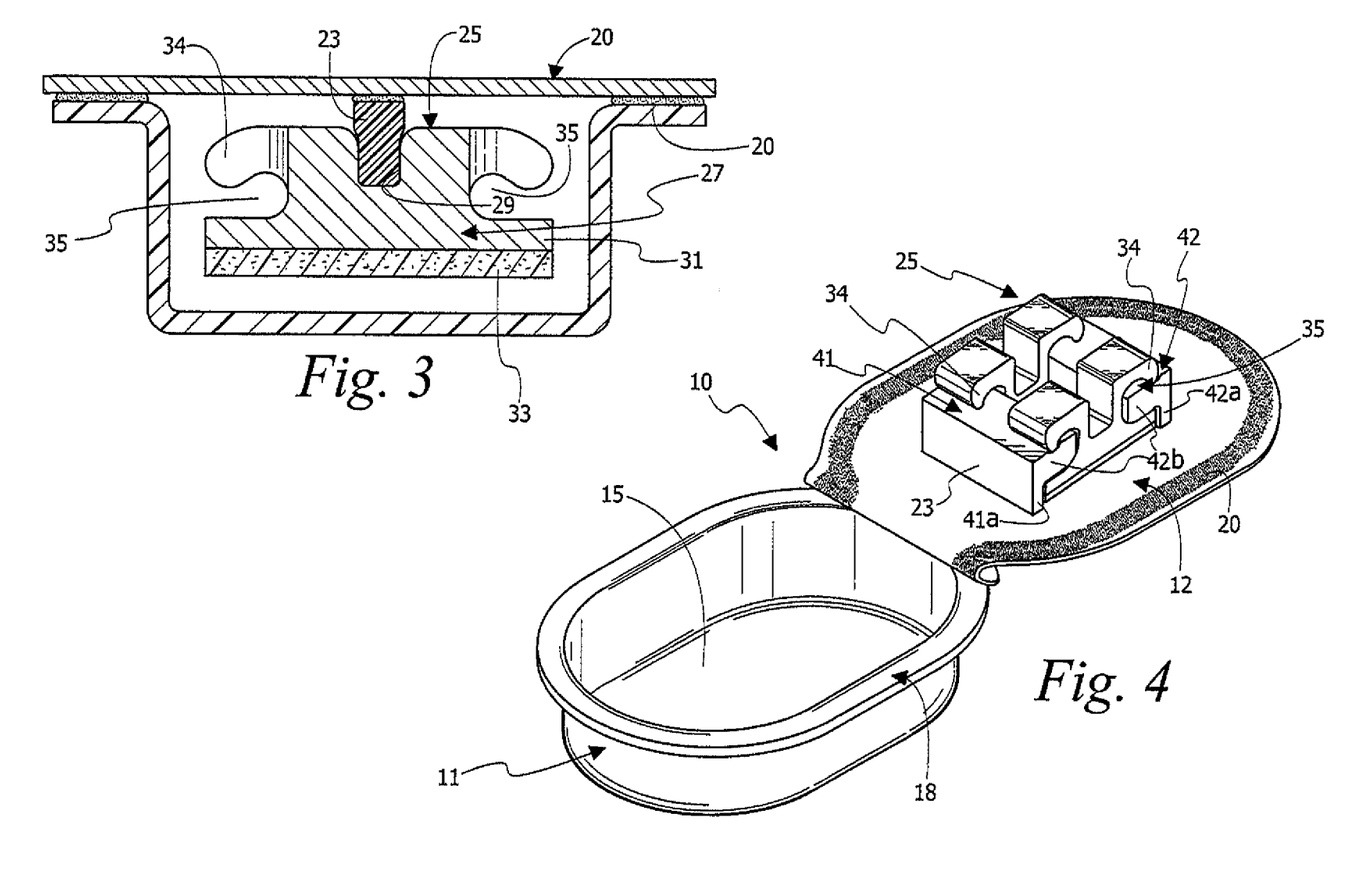
FIG. 3 is an enlarged cross-sectional view of the pod of FIGS. 1 and 2 with the lid closed and showing the position of the prepasted appliance within the pod during shipping and/or storing thereof.
FIG. 4 is an enlarged perspective view of the modified pod wherein the lid is in open position to place the prepasted appliance in a position so that it can be removed from the lid wherein the means for engaging the appliance and in this case an orthodontic bracket frictionally engages in the areas between the tie wings and the base.

Referring to the drawings, one embodiment of the invention is shown in FIGS. 1 to 3 wherein the pod is generally designated by the numeral 10 which includes a box or container generally indicated by numeral 11 and a lid or cover generally indicated by the numeral 12. The shape of the box or container 11 is oblong although it would be appreciated it could be of any suitable geometric shape, such as circular, square or rectangular if desired, and it can be formed particularly for that type of appliance that is to be shipped in the container.

The box or container 11 includes a bottom wall 15 and a side wall 17 and an upper lip 18 extending around the upper edges of the side wall 17, all integrally formed in a suitable manner such as by thermoforming or the like of a suitable plastic material that may be easily vacuumed formed to the shape of the box. For example, a high impact polystyrene material may be used although other types of material may be used depending upon the desires of the user and it would be appreciated that preferably the material will be opaque to light energy so that where an appliance includes a light curable adhesive or bonding material it will be protected against the light energy and maintain the uncured adhesive in a stable state during shipping and/or storage in the pod.

The lid 12 is formed so that it will cover the open end of the box and therefore have the same general outline as the outer part of the box, and it will be sized to fit on the lip 18 of the box. The cover or lid is of a suitable flexible material in the form of a film that may be easily positioned on the container of the pod for closing the upper open end of the pod. The film may be of a flexible polyester or the like. Preferably the lid is permanently attached to the lip 18 at the rear end to form a hinge so that the lid may be opened and closed on that hinge during the opening and closing of the container. A strip of repositionable or other pressure-sensitive adhesive 20 is arranged near the edge of the lid and in alignment so that when the lid is in closed position it will engage the lip 18 and maintain the lid in closed and sealed position until it is opened by a user. It will be appreciated the adhesive may be applied to the lip 18 of the pod.

In order to retain an orthodontic appliance on the underside of the lid 12 a bar 23 of a suitable compressible or resilient material such as expanded polystyrene is suitably secured in place to the lip and which would be sized to be slightly compressed and engagable in an archwire slot of a bracket as shown in FIG. 1 thereby retaining the prepasted bracket in position on the lid when moving the lid from open to closed position particularly as shown in FIG. 3 where it is in closed position and it is seen that the bracket 25 is suspended within the compartment of the pod such that the uncured adhesive will not engage the side or bottom walls of the container. For illustrative purposes, the orthodontic bracket 25 includes a body 27 having an outwardly opening edgewise archwire slot 29 on the base 31 for receiving round or edgewise wire.

The orthodontic bracket shown in connection with the pod is a twin-wing edgewise bracket of the usual type although it will be appreciated that it could be of any suitable type with one or more tie wings and include an archwire slot for engagement with the bar 23 of compressible material. It also could be a self-ligating bracket. The bracket 25 includes a base 27 having a body with an archwire slot 29 and tie wings 34. On the bottom of the base a layer of uncured bonding adhesive 33 is provided which by proper positioning and supporting within the pod, the adhesive is protected against engagement of the interior surfaces of the walls of the compartment of the pod and the cover during shipping and/or storage. The tie wings 34 form with the base openings 35 at each side of the bracket that are used for mounting the bracket on the cover member in the second embodiment shown in FIGS. 4 to 6. Thus it will be appreciated that any sort of means may be provided on the underside of the lid for frictionally engaging the parts of the bracket in order to frictionally and removably retain the bracket on the cover or lid during shipping and/or storage.

It should be appreciated that the shape of the bracket shown herein is for illustrative purposes for showing how a bracket may be removably attached to the lid of the pod. The archwire slot may be at an angle and the wings may be rhomboidally shaped or of any configuration that is normally used in the practice of orthodontia. Moreover the base while shown to be straight could have a curvature to match the curvature of the tooth on which it is to be mounted.

With regard to the operation of the pod, when a bracket or appliance is loaded into the pod, the lid is lifted from the end opposite the hinged area where a tab, although not shown, may be provided to facilitate and indicate where to lift the lid. The lid is hinged on the end which is permanently attached to the pod member 11 whereby the lid is lifted up and folded back as shown in FIGS. 1 and 2 to expose the interior of the pod and the compartment or cavity within the pod. The bracket or appliance is removably attached to the lid as shown in FIG. 1 wherein the bar 23 of compressible material is compressed and frictionally engaged by the archwire slot of the bracket 25.

The bracket as illustrated includes the body 27 having the base 31 and spaced therefrom tie wings 34. It can be appreciated that the bracket may have one or any number of tie wings. Generally a twin tie wing bracket is used by most practitioners except on single tie wing may be needed.

Between the tie wings and the base, openings 35 are normally provided and which will be utilized specifically in the embodiment of FIG. 4 for frictionally attaching the bracket to the cover or lid by hanging members.

When loading the bracket 25 onto the lid 12 or removing it from the lid, the bracket is preferably handled by a pair of tweezers or forceps 37 as shown in FIG. 2. The brackets are very small in size, and the bracket 25 may be engaged by the forceps either in the areas between the tie wings and the base as shown in FIG. 2 or by engaging the sides of the base. As above mentioned the bar 23 constitutes a means for frictionally retaining the bracket in place on the cover and this bar is made of a compressible material that is resilient in form and when once compressed will tend to return to its original shape and grip the bracket in the area of the archwire slot. With respect to the bar 23 of compressible resilient material, it can be appreciated that it can be made of any suitable material that is compressible and that will retain its shape and which will be capable of being permanently connected to the cover or lid 12 by such a means of a suitable adhesive when it is completely assembled. The width of the bar will be greater than the width of the archwire slot of the bracket and it will be preferably as long as the archwire slot so that it provides a good purchase or gripping of the bracket when it is mounted on the cover. Thus, it will be sized so that it will fully frictionally grip the bracket in the archwire slot area but be capable of being removed from the bar by applying a suitable force when it is time to remove the bracket from the cover and mount it onto a tooth. With respect to the embodiment of FIGS. 1 to 3 it will be necessary once the forceps 37 are gripping the bracket to turn the bracket over so that the bonding adhesive side of the bracket will face the tooth and be applied directly to the labial surface of a tooth. Once it is on the tooth it can be easily aligned and further positioned, and then bonded to the tooth by curing the uncured adhesive.

As previously mentioned the lid is permanently attached to the lip 18 of the box 11 thereby providing a hinge for the lid as it is opened and closed relative to mounting a bracket on the bar 23 to frictionally attach the bracket to the cover or removing it from the bar to mount on a tooth.

Figures 5, 6:
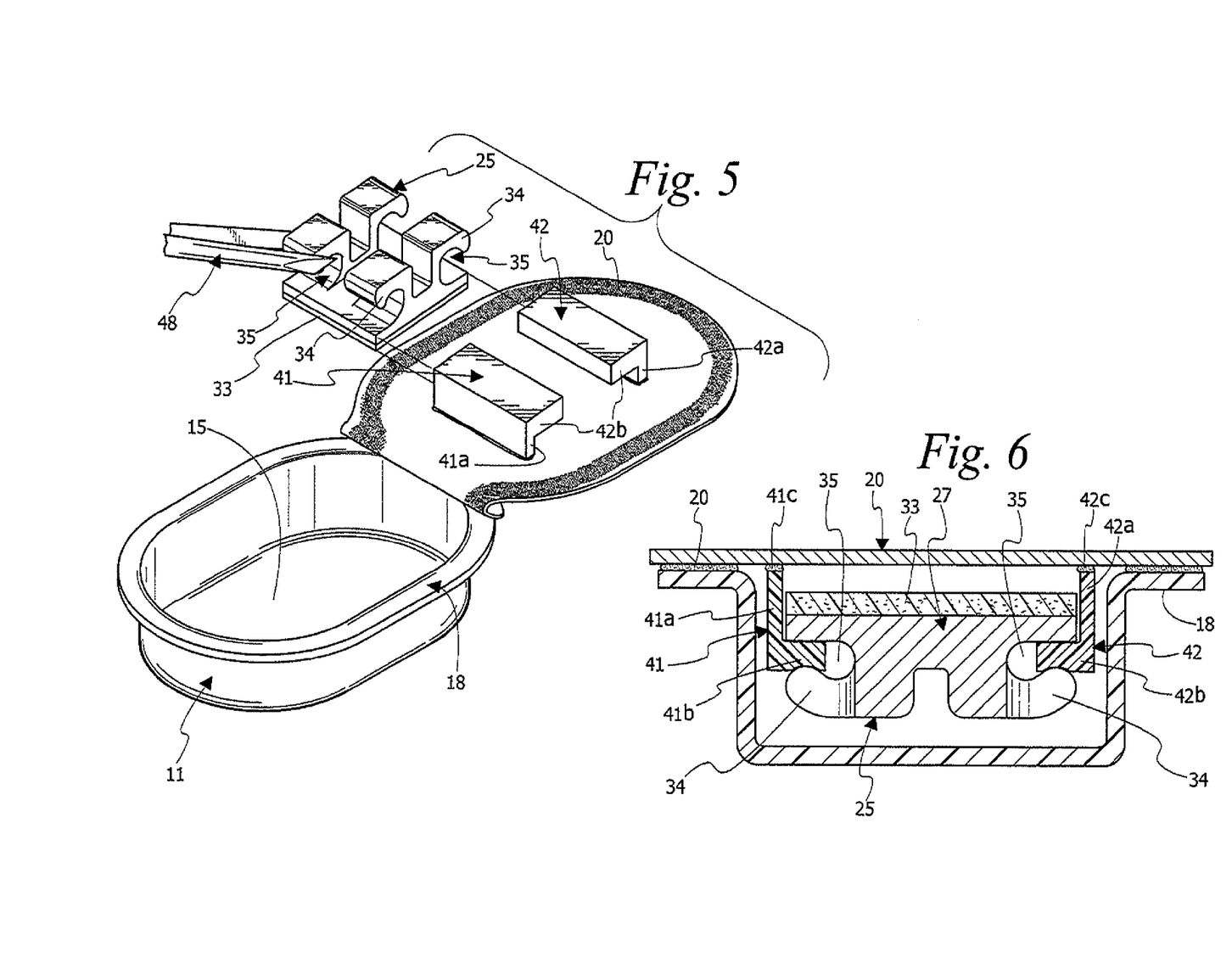
FIG. 5 is an enlarged perspective view of the embodiment of FIG. 4 and showing an instrument engaging the prepasted bracket and in a removed position from the retaining means on the lid.
FIG. 6 is an enlarged cross-sectional view of the embodiment of FIGS. 4 and 5 wherein the lid is closed and illustrating the manner in which the appliance is mounted within the pod during shipment and/or storage.

Another embodiment of the invention is shown in FIGS. 4, 5 and 6 wherein the underside of the lid 12 is provided with a pair of L shaped hanging members 41 and 42 as shown on FIGS. 5 and 6. Each hanging member includes a vertical component or bar 41a or 42a and a horizontal component or bar 41b or 42b. As particularly seen in FIG. 6 the ends of the bars 41a and 42a are permanently adhesively attached to the underside of the cover by means of adhesive 41c and 42c. It will be appreciated that the L shaped hangers 41 and 42 will be spaced apart as seen in FIG. 6 such that they can engage in the opposite sides of the bracket at the occlusal and gingival edges as shown in FIG. 6. The horizontal elements 41b and 42b are sized larger than the openings 35 between the base and the tie wings so that when the bracket is mounted on the L shaped hangers it will cause the squeezing of the elements 41b and 42b so as to frictionally engage the bracket with respect to the hangers.

It will be understood that the brackets would be slidably positioned on the hangers and thereafter removed from the hangers by a suitable tool such as the forceps shown in FIG. 5 and generally designated by the numeral 48. The forceps can engage an upper or lower tie wing tip to grip the bracket and move it on or off of the hangers on the cover member. In this embodiment it will be noted that the bracket, when exposed from within the pod and when the lid is folded back on its hinge, will be in an upright position whereby the bracket when removed from the pod lid can be placed directly on a tooth without having to turn the bracket over as in the embodiment of FIGS. 1 to 3. It will also be appreciated that the bracket in this embodiment will be frictionally engaged by the hanging means when it is mounted on the lid of a cover and thereafter it will be supported within the pod as seen particularly in FIG. 6 so that the tie wings do not engage the bottom wall of the pod and the adhesive coated base will not engage the lid or be disturbed by the lid during the shipping and/or storing of the bracket within the pod.

While it is not necessary to reshape the pod of the embodiment of FIGS. 4 to 6 and it may take the same shape as the pod of FIGS. 1 to 3, it can be appreciated that it may be either circular, square or rectangular in shape depending upon the desires of the user. However it will be appreciated that the means for frictionally engaging the bracket to support and removably hold the bracket during shipment and/or storage will be of a different configuration than that of the embodiment of FIGS. 1 to 3.

Figures 7, 8:
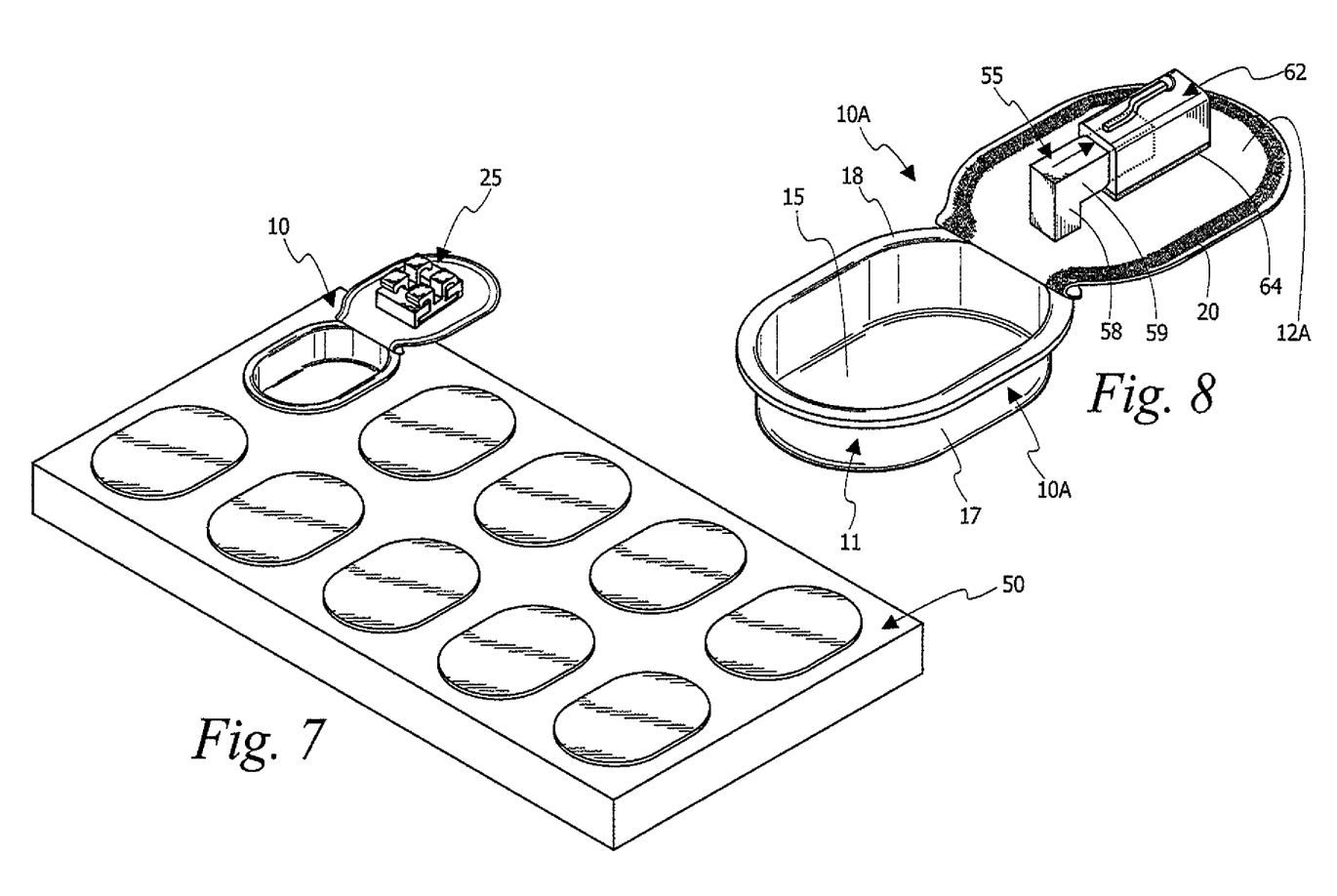
FIG. 7 is an enlarged perspective view of a carrier or tray having multiple pods for providing a system of prepasted appliances for use by the orthodontist and showing the cover of one pod in open position exposing an orthodontic bracket functionally mounted on the cover retaining means.
FIG. 8 is an enlarged perspective view of a modified pod for use in shipping a buccal tube wherein the tube is partially removed from the cover retaining means.

As above mentioned the pods may be shipped in singular form as shown in FIGS. 1 and 6 or they may be shipped on a carrier or tray in multiple form as shown in FIG. 7 wherein a tray 50 is provided with a plurality of openings into which a pod may be inserted for positioning on the tray, thus a plurality of pods with brackets of a particular system may be shipped on a single tray. The pods may be loaded onto the tray after they have the brackets in place therein, or they may be loaded on the tray prior to the placement of brackets in the pods. Suitable legends or markings will be made on the pod covers or tray to identify the bracket in the pod. In any event it can be appreciated that a plurality of the pods may be shipped as a unit as seen in FIG. 7 if so desired which would have a row of pods for upper and lower teeth and for the various teeth that are provided in a patient.

Referring now to the pod shown in FIG. 8 which is generally designated by the numeral 10A, this pod differs only in that it provides an L-shaped hanger 55 mounted under the cover for shipping or storing a buccal tube rather than a bracket. The hanger 55 includes a vertical section 58 and a horizontal section 59 wherein the horizontal section is sized to be received in an opening of a buccal tube 62. While the entire hanger may be made of compressible material, it will be appreciated that only the section 59 that engages the opening in the tube need be compressible. It will be appreciated that the horizontal arm 59 of the hanger 55 is sized to be larger than the opening in the buccal tube so that when the buccal tube is mounted on this arm it will cause a compression of the arm material within the buccal tube such that the tube is in frictional engagement with the hanger and will be held it in place during shipping when the cover is closed. The hanger 55 is therefore permanently mounted on the underside of the lid 12A and when the cover is closed with the buccal tube in place it will cause the uncured adhesive layer 64 to be suspended as to not engage the lid and therefore will be protected against being disturbed during shipping and/or storing of the buccal tube in the pod. Alternately, the buccal tube may be mounted on the hanger so the adhesive side of the tube would face the bottom of the pod when the lid is closed.

It will be appreciated that other types of appliances having a prepasted bonding base may also be shipped in the pod of the invention and the means for frictionally engaging the appliance will be designed so that it will be engaging the appliance in such a way that the uncured adhesive base will not engage any of the walls of the pod and the appliance will be suspended in air.

While the invention has been described with respect to certain preferred embodiments, as will be appreciated by those skilled in the art, it is to be understood that the invention is capable of numerous changes, modifications and rearrangements and such changes, modifications and rearrangements are intended to be covered by the following claims.

The invention claimed is:

1. A pod for shipping and/or storing a prepasted orthodontic bracket having a body with a base,
    said body including tie wings extending from said base, and an outwardly opening archwire slot between the wings for receiving an archwire and,
    a layer of uncured adhesive on the base for bonding the bracket to a tooth,
    said pod including a compartment having bottom and side walls and an open top into which the bracket may be received, and a lid attached to said pod for opening and closing the compartment, said lid comprising an underside facing the compartment when closed,
    and a retention means mounted on the underside of the lid that has a friction fit with the archwire slot, such that when the lid is open the retention means will remove the bracket by attachment to the archwire slot.

2. The pod of claim 1,
    wherein said retention means comprises a blade of compressible material frictionally engaging in the archwire slot of the bracket.

3. The pod of claim 1,
    wherein said retention means comprises elements of compressible material engaging between the tie wings and the base of the bracket.

4. A package for a prepasted bracket comprising a carrier having at least one pod within which a bracket may be received,
    said bracket including an upper side having opposed tie wings and an archwire slot therebetween, a bottom side having a base, opposed edges, and an uncured bonding adhesive on the base,
    said pod having a bottom wall and sidewalls extending upwardly from the bottom wall defining a compartment with an opening into which a bracket may be inserted into or removed therefrom, and
    cover means attached at an end thereof to said pod and movable between open and closed positions for enclosing the opening when in closed position,
    said cover means including a retention means mounted on the underside of the cover means that has a friction fit with the archwire slot, such that when the cover means is open the retention means will remove the bracket by attachment to the archwire slot, the retention means supporting said bracket within the pod such that the bonding adhesive on said base does not touch said bottom wall and sidewalls,
    whereby the bracket is inhibited from moving in the pod during shipping and upon opening the cover means presents the bracket for removal from the cover means and be readily available for mounting on a tooth.

5. The package of claim 4,
    wherein said cover means in closed position is secured to said pod with repositionable adhesive.

6. The package of claim 4,
    wherein said means extending from the cover to support the bracket during shipping includes a bar of compressible material engaging in said archwire slot.

7. The package of claim 6,
    wherein said bar is wider than the archwire slot prior to engagement with said slot.

8. The package of claim 4,
    wherein said means extending from the cover means includes elements of compressible material engaging between said tie wings and base.

9. A package for shipping and/or storing an orthodontic appliance,
    said appliance comprising a body which defines an archwire slot and a prepasted base with a layer of uncured adhesive on the base for bonding the appliance to a tooth,
    said package including a compartment into which the appliance may be inserted and withdrawn therefrom,
    said compartment being defined by side and bottom walls,
    and a lid having inner and outer sides and being attached to said compartment along one edge thereof for closing the compartment and further comprising a retention means mounted on the inner side of the lid that has a friction fit with the archwire slot, such that when the lid is open the retention means will remove the bracket by attachment to the archwire slot, the retention means suspending the appliance in the compartment from the lid when the lid is closed so that the adhesive on the base will not touch said side and bottom walls, whereby lifting of the lid to open the compartment withdraws the appliance therefrom so that it can be grasped and removed from the lid and directly mounted on a tooth.

10. The package of claim 9, wherein said appliance is a bracket.

11. The package of claim 10, wherein said appliance is a buccal tube.

12. The package of claim 10, wherein said appliance is a lateral attachment.

* * * * *